(12) United States Patent
Anumula

(10) Patent No.: US 6,800,486 B1
(45) Date of Patent: Oct. 5, 2004

(54) METHOD FOR QUANTITATIVE DETERMINATION OF AMINO ACIDS

(75) Inventor: Kalyan R Anumula, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/857,580

(22) PCT Filed: Dec. 7, 1998

(86) PCT No.: PCT/US99/28992

§ 371 (c)(1),
(2), (4) Date: Jun. 7, 2001

(87) PCT Pub. No.: WO00/34251

PCT Pub. Date: Jun. 15, 2000

Related U.S. Application Data

(60) Provisional application No. 60/111,250, filed on Dec. 7, 1998.

(51) Int. Cl.[7] .................. C07D 263/58; C07K 1/113; C07K 1/13; G01N 21/63; G01N 21/64
(52) U.S. Cl. ..................... 436/89; 436/90; 530/345; 530/409; 548/222
(58) Field of Search ................ 436/89, 90; 530/345, 530/409; 548/222

(56) References Cited

U.S. PATENT DOCUMENTS

| 4,814,459 A | 3/1989 | Boesenberg et al. ........ 548/161 |
| 5,296,486 A | 3/1994 | Lazer et al. ................ 514/333 |

OTHER PUBLICATIONS

Advani, et al. Potential Antineoplastic Agents: N–(2–Benzoxazolyl)amino Acid Esters. Journal of Pharmaceutical Sciences. Oct. 1968, vol. 57, No. 10, pp. 1693–1696, especially Table I, p. 1695, col. 1, paragraph bridging pp. 1695 and 1696.

Langguth et al. Fluorescence Assay . . . Journal of Chromatography. 1990, vol. 528, pp. 55–64.

Primary Examiner—Jeffrey Edwin Russel
(74) Attorney, Agent, or Firm—Soma G. Simon; Mary E. McCarthy; Charles M. Kinzig

(57) ABSTRACT

A novel method for the determination of amino acids by HPLC using pre-column derivatization is described. In this procedure, the aminno acids are derivatized with 2-chlorobenzoxazole to yield highly fluroresent N-(2-benzoxazolyl)-amino acids (BOX-AAs) for detection at very high sensitivity. Derivatives can also be detected using conventional UV detection methods. The BOX-AAs can be separated on a C18 reversed phase column for quantitative estimation. This method can be used for the preparation of N-(2-benzoxazolyl)-amino acids in large amounts.

1 Claim, 1 Drawing Sheet

METHOD FOR QUANTITATIVE DETERMINATION OF AMINO ACIDS

This application claims the benefit of provisional application 60/111,250 filed Dec. 7, 1998.

FIELD OF THE INVENTION

The present invention is directed to methods for the quantitative determination of amino acids.

SUMMARY OF THE INVENTION

The present invention is directed to a novel method for derivatizing amino acids or peptides, which method comprises reacting an amino acid or peptide with a fluorescent benzoxazole derivative, such as 2-chlorobenzoxazole.

The present invention is also directed to a method of detecting, qualitatively and quantitatively, amino acids and peptides, which method comprises reacting an amino acid or peptide with 2-chlorobenzoxazole and detecting the resultant derivative by a suitable method, such as UV or fluorescence methods.

The present invention also relates to the novel benzoxazole- amino acid derivatives, N-(2-benzoxazolyl) amino acids as described herein.

DETAILED DESCRIPTION OF THE INVENTION

Figure 1:
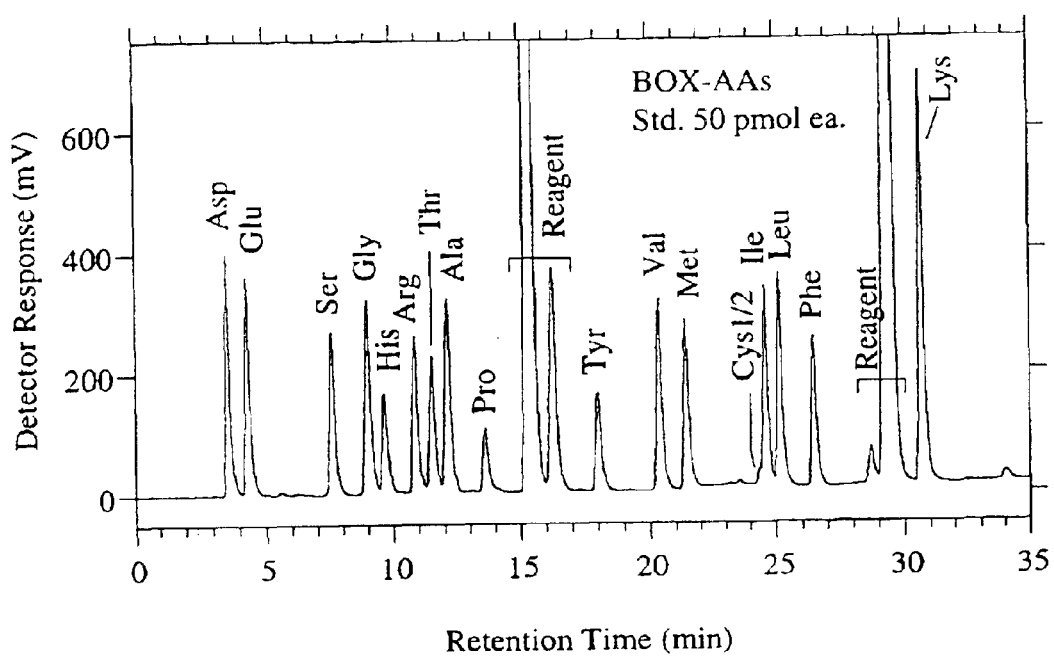
FIG. 1 provides for the results of amino acid separation of N-(2-benzoxazolyl)-amino acids on a Beckman C18 column. The amino acids in the chromatogram were identified by derivatizing and analyzing the commercial amino acids individually.

Currently, amino acid analysis is routinely performed using HPLC with pre- and post-column derivatization chemistry for enhanced sensitivity. The present invention is directed towards the use of highly fluorescent N-(2-benzoxazole) derivatives, in particular 2-chlorobenzoxazole (CBOX) as a sensitive, fluorescent tag for the quantitative determination of amino acids. CBOX is readily available from commercial sources, such as Aldrich Chemicals.

The present invention is directed towards use of the fluorescent N2-benzoxazolyl)-amino acids (BOX-AAs) derivatives in determination of the amino acids by HPLC using pre-column derivatization as described herein. In this procedure, the amino acids are derivatized with the CBOX to yield the highly fluorescent N-(2-benzoxazolyl)-amino acids (BOX-AAs) for detection at very high sensitivity. The derivatives can also be detected using conventional UV detection methods. The BOX-AAs can be separated on a C18 reversed phase columns for quantitative estimation. This method can be used for the preparation of N-(2-benzoxazolyl)-amino acids in large amounts.

Generically the amino acid standards and samples are derivatized with a BOX reagent, preferably CBOX in an alkaline medium, such as sodium carbonate, to yield a stable fluorescent amino acid derivative, which is separated by reversed phase chromatograph (Ultrasphere-ODS, 0.4×25 cm, Beckman). All of the BOX-AA are baseline resolved within 35 minutes or so. Peak areas for the BOX-AA are similar except for Pro (45%), Tyr and His (60%) and Lys (200%), presumably due to an additional amine group.

The invention will now be described by reference to the following examples which are merely illustrative and are not to be construed as a limitation of the scope of the present invention. All temperatures are given in degrees centigrade and all solvents are highest available purity.

Experimental

Preparation of the Derivalizing Solution

An aqueous solution of 0.1–5% sodium acetate tri-hydrate (w/v) was prepared first. Fifty uL of this solution is mixed with 1.0 mL of methanol. Chlorobenzoxazole (10–50 uL) was mixed with methanol-sodium acetate solution.

Derivatization of Amino Acids

Amino acid standards (1.0 nmol each from Pierce) in 50 uL of buffer (for e.g. 0.25 M sodium carbonate) was mixed with 100 uL of the above 2-chlorobenzoxazole solution for derivatization. The reaction was allowed to continue typically at 80° C. for 10–60 min. After the reaction, the samples were diluted with sodium acetate solution and an aliquot was injected onto HPLC for analysis.

Proteins were hydrolyzed with 6N hydrochloric acid and the dried hydrolysates were derivatized in a manner similar to amino acid standards.

Separation of Amino Acids

The derivatized amino acids were separated on a C18 reversed phase column. Typical solvent consisted of A: 2% ammonium bicarbonate (0.1–2% w/v) in 20% methanol-water and B: 1–20% methanol in acetonitrile. The amino acids were separated with a gradient generated from these solvents. A typical gradient consisted of 5% B isocratic for 8 min followed by a linear gradient to 45% B over 35 min.

Results

Reaction scheme for amino acid derivatization with 2-chlorobenzoxazole to yield 2-benzoxazole derivatives is shown in Scheme I.

2-Benzoxazole derivatives can be detected using either UV or fluorescence. An excitation and emission maxima of 245 nm and 320 nm respectively were used for fluorescence detection. Separation of BOX-AAs on a Beckman C18 (ODS Ultrasphere, 0.46×25 cm) is shown in FIG. 1.

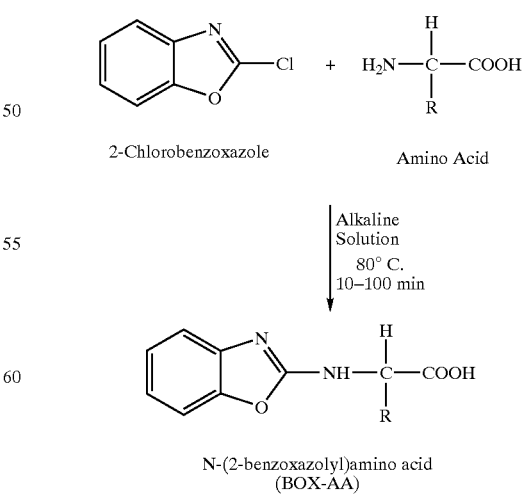

2-Chlorobenzoxazole          Amino Acid

Alkaline Solution
80° C.
10–100 min

N-(2-benzoxazolyl)amino acid
(BOX-AA)

Fluorescence: 245 nm ex. and 320 nm em.

As an alternative to 2-Chlorobenzoxazole, a reagent of formula (1) may also be used:

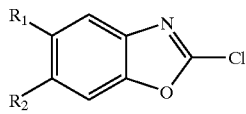

(I)

wherein $R_1$ and $R_2$ are independently selected from the group consisting of hydrogen, halo and $C_{1-4}$hydroxy.

Scheme I. Reaction scheme for the formation of 2-benzoxazolyl-AAs.

Another aspect of the present invention are the specific derivatized amino acid derivatives with a benzoxazole derivative, i.e., N-(2-benzoxazolyl) amino acids. The commonly used, well known amino acids encompassed by this description include:

| Abbreviation | Amino acid name |
|---|---|
| Ala | Alanine |
| Arg | Arginine |
| Asn | Asparagine |
| Asp | Aspartic Acid |
| Asx | Aspartic Acid or Asparagine |
| Cys | Cysteine |
| Glu | Glutamic Acid |
| Gln | Glutamine |
| Glx | Glutamine or Glutamic Acid |
| Gly | Glycine |

| Abbreviation | Amino acid name |
|---|---|
| His | Histidine |
| Ile | Isoleucine |
| Leu | Leucine |
| Lys | Lysine |
| Met | Methionine |
| Phe | Phenylalanine |
| Pro | Proline |
| Ser | Serine |
| Thr | Threonine |
| Trp | Tryptophan |
| Tyr | Tyrosine |
| Val | Valine |

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A method of detecting amino acids and peptides, which method comprises reacting an amino acid or peptide with 2-chlorobenzoxazole and detecting the resultant derivative by UV or fluorescence methods.

* * * * *

SEQUENCE LISTING

```
<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Ala Arg Asn Asp Asx Cys Glu Gln Glx Gly His Ile Leu Lys Phe Pro
1               5                   10                  15

Ser Thr Trp Tyr Val
            20

<210> SEQ ID NO 2
<211> LENGTH: 17
<212> TYPE: PRT
<213> ORGANISM: Artificial Sequence
<220> FEATURE:
<223> OTHER INFORMATION: Amino acids derived from 2-chlorobenzoxazole
      to yield highly fluorescent N-(2-benzoxazolyl)-amino acids for
      detection at very high sensitivity.
```

-continued

```
<400> SEQUENCE: 2

Asp Glu Ser Gly His Arg Thr Ala Pro Tyr Val Met Cys Ile Leu Phe
1               5                  10                 15
Lys
```